(12) United States Patent
Merfeld et al.

(10) Patent No.: US 7,962,217 B2
(45) Date of Patent: Jun. 14, 2011

(54) VESTIBULAR STIMULATOR

(75) Inventors: Daniel M. Merfeld, Lincoln, MA (US);
Wangsong Gong, Revere, MA (US);
Steven D. Rauch, Watertown, MA (US);
Conrad Wall, III, Boston, MA (US)

(73) Assignee: Massachusetts Eye & Ear Infirmary,
Boston, MA (US)

( * ) Notice: Subject to any disclaimer, the term of this patent is extended or adjusted under 35 U.S.C. 154(b) by 819 days.

(21) Appl. No.: 11/351,388

(22) Filed: Feb. 9, 2006

(65) Prior Publication Data

US 2006/0129206 A1 Jun. 15, 2006

Related U.S. Application Data

(62) Division of application No. 10/738,920, filed on Dec. 16, 2003, now Pat. No. 7,933,654.

(60) Provisional application No. 60/433,946, filed on Dec. 17, 2002.

(51) Int. Cl.
*A61N 1/36* (2006.01)
(52) U.S. Cl. ................... 607/45; 607/2; 607/55
(58) Field of Classification Search .............. 607/42, 607/45, 55, 56, 137
See application file for complete search history.

(56) References Cited

U.S. PATENT DOCUMENTS

| 4,535,777 | A | | 8/1985 | Castel | |
|---|---|---|---|---|---|
| 4,558,703 | A | * | 12/1985 | Mark | 607/72 |
| 4,667,676 | A | | 5/1987 | Guinta | |
| 4,754,748 | A | | 7/1988 | Antowski | |
| 4,984,579 | A | * | 1/1991 | Burgert et al. | 600/560 |
| 5,658,322 | A | | 8/1997 | Fleming | |
| 5,891,182 | A | | 4/1999 | Fleming | |
| 5,919,149 | A | | 7/1999 | Allum | |
| 6,063,046 | A | | 5/2000 | Allum | |
| 6,078,838 | A | | 6/2000 | Rubinstein | |
| 6,219,578 | B1 | | 4/2001 | Collins et al. | |
| 6,234,953 | B1 | * | 5/2001 | Thomas et al. | 600/14 |
| 6,295,472 | B1 | | 9/2001 | Rubinstein et al. | |
| 6,314,324 | B1 | | 11/2001 | Lattner et al. | |
| 6,430,443 | B1 | | 8/2002 | Karell | |
| 6,600,954 | B2 | * | 7/2003 | Cohen et al. | 607/46 |
| 2002/0072781 | A1 | | 6/2002 | Lattner et al. | |
| 2003/0195588 | A1 | | 10/2003 | Fischell et al. | |
| 2004/0215236 | A1 | | 10/2004 | Lattner et al. | |

OTHER PUBLICATIONS

Netter, Frank H., "Atlas of Human Anatomy," 2003, ICON Learning Systems, Third Edition, plates 87 and 91.*
Sadeghi, Soroush G. et al, "Response of Vestibulr-Nerve Afferents to Active and Passive Rotations Under Normal Conditions and After Unilateral Labyrinthectomy", Nov. 22, 2006, J. Neurophysiol, 97:1503-1514.*
Meiry, Jacob L., "The Vestibular System and Human Dynamic Space Orientation", Oct. 1966, NASA Contractor Report, NASA CR-628.*
"Prototype Neural Semicircular Canal Prosthesis Using Patterned Electrical Stimulation" by W. Gong and D. M. Merfeld, Annals of Biomedical Engineering, vol. 28, pp. 572-581, 2000.

(Continued)

*Primary Examiner* — Michael Kahelin
(74) *Attorney, Agent, or Firm* — Occhiuti Rohlicek & Tsao LLP

(57) ABSTRACT

A method for providing relief from Meniere's disease, includes reversibly disabling vestibular function following detection of an attack of Meniere's disease following detection of an attack of Meniere's disease.

20 Claims, 4 Drawing Sheets

OTHER PUBLICATIONS

"Vestibular Function and Anatomy" by C. Wall III and J. T. Vrabec, Department of Otolaryngology-Head and Neck Surgery, University of Texas Medical Branch, Galveston, TX, pp. 1891-1901.

"System Design and Performance of a Unilateral Horizontal Semicircular Canal Prosthesis" by Gong et al., IEEE Transactions on Biomedical Engineering, vol. 49, No. 2, Feb. 2002, pp. 175-181.

"Vestibular Function and Anatomy" by C. Wall III and J. T. Vrabec, Department of Otolaryngology-Head and Neck Surgery, University of Texas Medical Branch, Galveston, TX, pp. 1891-1901, 1998.

Jewell. "How to Prevent and Alleviate Dizziness". eHow. http://www.ehow.com/how_4561037_alleviate-dizziness.html (Retrieved Oct. 20, 2009) (1 page).

"How to Use Chrysanthemums to Cure Vertigo" eHow. http://www.ehow.com/how_2257288_use-chrysanthemums-cure-vertigo.html (Retrieved Oct. 20, 2009) (1 page).

Cass, Diane. "How to Cure Vertigo" eHow. http://www.ehow.com/how_4697040_cure-vertigo.html (Retrieved Oct. 20, 2009)(2 pages).

C. Claiborne Ray. "The Merry-Go-Round Effect" *The New York Times*. (Retrieved Oct. 29, 2009) Oct. 27, 2009 (1 page).

\* cited by examiner

VESTIBULAR STIMULATOR

RELATED APPLICATION

This application is a divisional of pending U.S. application Ser. No. 10/738,920, U.S. Pat. No.7,933,654 filed Dec. 16, 2003, which claims the benefit of the priority date of U.S. provisional application 60/433,946, filed Dec. 17, 2002 the contents of which are incorporated herein by reference.

FIELD OF INVENTION

This invention relates to treatment for vestibular dysfunction.

BACKGROUND

When a normal person is stationary, the neurons associated with the vestibular system carry pulse trains that, on average, have a nearly constant pulse-repetition frequency. If the patient changes spatial orientation, the average pulse-repetition frequency of the pulse trains changes. These pulse trains, hereafter referred to as the "vestibular signal", are transmitted to the brain via the vestibular nerve. On the basis of changes in the average pulse-repetition frequency, the brain determines the patient's spatial orientation and motion.

The vestibular system is not the brain's only source of information concerning the patient's spatial orientation. Both the vision and other sensory systems, such as the proprioceptive and tactile systems, provide additional cues. The brain reconciles these additional cues with information from the vestibular system. To the extent that these cues are inconsistent with each other, the patient experiences dizziness.

In one afflicted with Meniere's disease, the vestibular system, for no apparent reason, suddenly begins varying the pulse-repetition frequency of the vestibular signal even when the patient is stationary. This results in severe dizziness. Then, and again for no apparent reason, the vestibular system begins generating a vestibular signal consistent with the person's spatial orientation, thereby ending the person's symptoms.

Known treatments for Meniere's disease include surgical removal of the patient's vestibule. Another treatment involves perfusion of ototoxic drugs that permanently destroy the cilia within the vestibule. As a result, these treatments result in the permanent loss of the patient's sense of balance.

Less draconian treatments for Meniere's disease include the introduction of drugs having questionable efficacy, acupuncture, and various homeopathic remedies. These treatments have not shown consistent success.

SUMMARY

In one aspect, the invention includes an apparatus for stimulating the vestibular system. The apparatus includes an actuator disposed to interact with the vestibular nerve and a controller for causing the actuator to interact with the vestibular nerve. The result of the interaction is that the brain receives a stationary signal.

Embodiments of the invention include those in which the actuator has an implantable electrode, an antenna, an external electrode, an implantable electrode having a receiver for communication with a transmitter outside the patient, or a magnetic field source, each of which is in communication with the vestibular nerve. Other embodiments include those in which a vibrating element is adapted to mechanically stimulate the vestibule.

Other embodiments of the invention include those in which the actuator includes a chemical delivery system adapted for delivering a chemical agent to an active region. Once in the active region, the chemical agent interacts with the vestibular nerve. Such a chemical delivery system might include, for example, a reservoir for containing the chemical agent, and a pump for delivering the chemical agent from the reservoir to the active region.

Some embodiments of the apparatus include an externally actuated switch in communication with the controller for enabling external control of an interaction with the vestibular nerve. In other embodiments, the apparatus includes a sensor adapted to detect a first signal on the vestibular nerve. Such a sensor is in communication with the controller for causing the controller to generate a second signal in response to the first signal.

In some embodiments, the controller is configured to cause the actuator to generate a signal that, when combined with a non-stationary signal present on the vestibular nerve, causes a stationary signal to be transmitted to the brain.

Another aspect of the invention is a method for providing relief from Meniere's disease by reversibly disabling vestibular function following detection of an attack of Meniere's disease.

In certain practices of the invention, reversibly disabling vestibular function includes temporarily causing the vestibular nerve to carry a stationary signal to the brain. This can be achieved, for example, by causing the vestibular nerve to carry a jamming signal that, when combined with a non-stationary signal present on the vestibular nerve, causes the vestibular nerve to carry a stationary signal to the brain. One example of a jamming signal is a pulse train having a selected pulse repetition frequency.

The jamming signal can be generated in a variety of ways, for example by electrical or electromagnetic stimulation of the vestibular nerve, by mechanically stimulating the vestibule, or by exposing the vestibular nerve to a chemical agent.

In one practice of the invention, the chemical agent is a neurotransmitter. However, the chemical agent can also be a nerve-impulse blocking agent.

In another practice of the invention, the method includes detecting onset of an attack of Meniere's disease, and applying a jamming signal following detection of an attack. Other practices of the invention include those in which the jamming signal is removed at the end of an attack of Meniere's disease.

Meniere's disease is episodic in nature. During an attack, the patient experiences severe discomfort. However, between attacks, the patient is largely asymptomatic. Conventional methods of treating Meniere's disease disable vestibular function permanently, thereby leaving the patient with no vestibular function even during asymptomatic periods. The invention provides relief from the disease by disabling vestibular function only during the attack itself, but not during the period between such attacks. As a result, the patient's vestibular function is available during asymptomatic periods.

Another aspect of the invention is a method for providing relief from hemineglect by isothermally stimulating vestibular function.

In certain practices of the invention, stimulating vestibular function includes causing the vestibular nerve to carry a stationary signal to the brain. This can be achieved, for example, by causing the vestibular nerve to carry a jamming signal that, when combined with a non-stationary signal present on the vestibular nerve, causes the vestibular nerve to carry a stationary signal to the brain. One example of a jamming signal is a pulse train having a selected pulse repetition frequency.

The jamming signal can be generated in a variety of ways, for example by electrical stimulation of the vestibular nerve, by mechanically stimulating the vestibule, or by exposing the vestibular nerve to a chemical agent.

In one practice of the invention, the chemical agent is a neurotransmitter. However, the chemical agent can also be a nerve-impulse blocking agent.

These and other features and advantages of the invention will be apparent from the following detailed description and the accompanying figures, in which:

DETAILED DESRCIPTION

Figure 1:
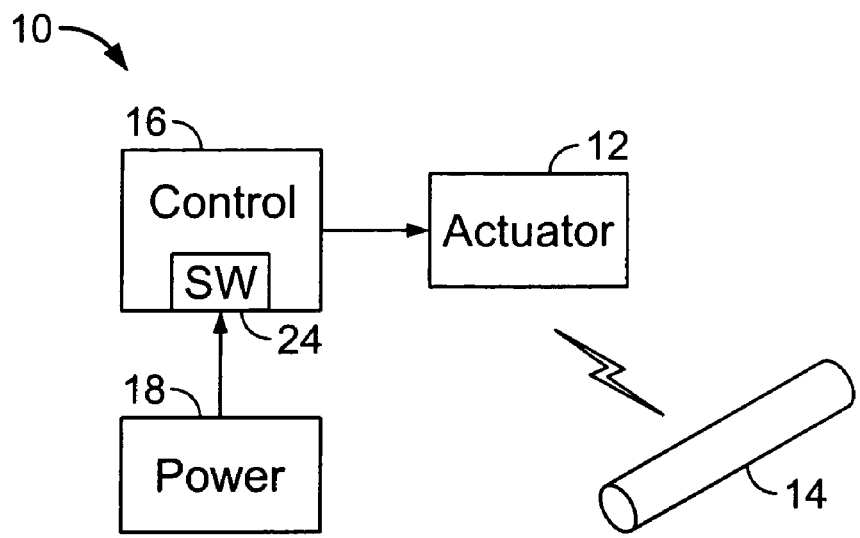
FIG. 1 is an apparatus according to the invention.

FIG. 1 shows an apparatus 10 for providing symptomatic relief from Meniere's disease. The apparatus includes an actuator 12 in communication with the vestibular nerve 14. A control unit 16 in electrical communication with the actuator 12 provides control over a jamming signal present at the actuator 12. As used herein, electrical communication encompasses both a wireless connection, in which communication is carried out by electromagnetic waves, and a wired connection. In one particular embodiment disclosed herein, this jamming signal is a pulse train having a controllable pulse amplitude and pulse-repetition frequency, both of which are set by the control unit 16. However, the jamming signal can also be any other time-varying stimulus. Examples of other jamming signals include sinusoidal signals or any other oscillatory signals.

A power source 18, such as a rechargeable battery, provides power to both the actuator 12 and the control unit 16.

During an attack of Meniere's disease, a vestibular signal on the vestibular nerve develops time-varying changes in the neural pulse-repetition frequency even when the patient's spatial orientation is not changing. A time-varying signal of this type, in which the amplitude or frequency is modulated with time, is often referred to as a "non-stationary" signal.

The patient interprets a non-stationary signal on the vestibular nerve as indicating a change in his spatial orientation, even when his spatial orientation has not changed at all. The vestibular signal, together with the mismatch between the vestibular signal and other motion cues available to the brain results in dizziness and discomfort.

The apparatus 10 relieves the discomfort of Meniere's disease by temporarily and reversibly disabling vestibular function. It does so by jamming the vestibular signal with the jamming signal. The characteristics of this are selected so that the combination of the jamming signal and the vestibular signal results in a signal having a constant pulse-repetition frequency. Examples of characteristics that can be selected to achieve this are the jamming signal's pulse amplitude and pulse-repetition frequency.

Proper selection of the jamming signal's characteristics causes the brain to receive a stationary signal instead of the non-stationary signal that characterizes Meniere's disease. To the extent that the patient remains stationary during the attack, the brain receives a signal consistent with the patient's constant spatial orientation. Since the brain now receives a signal consistent with other motion cues, the discomfort associated with Meniere's disease is alleviated.

Figure 2:
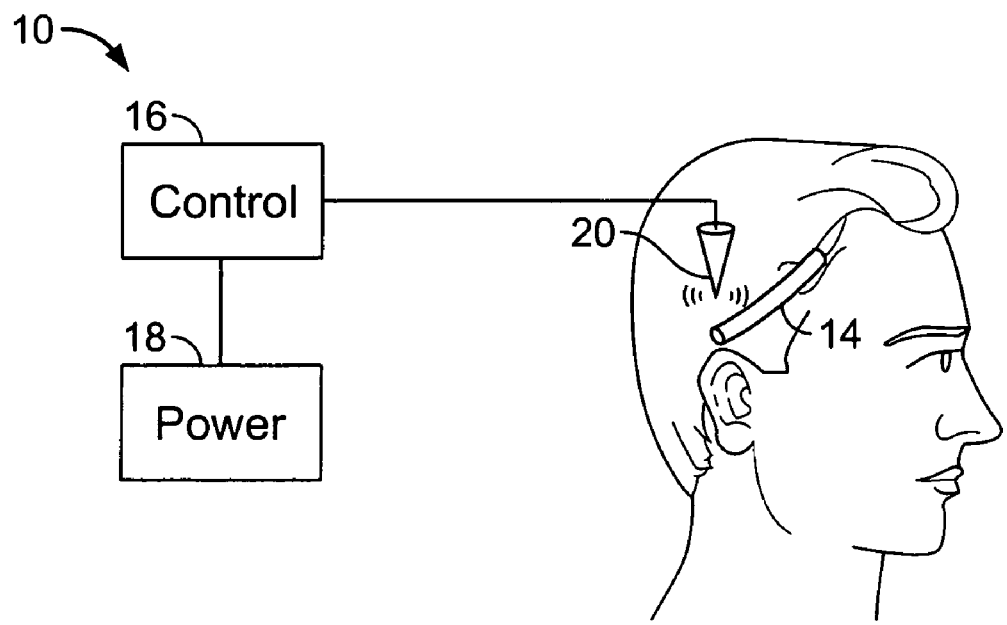
FIG. 2 is an embodiment in which the actuator of FIG. 1 is an electrode.
Figure 3:
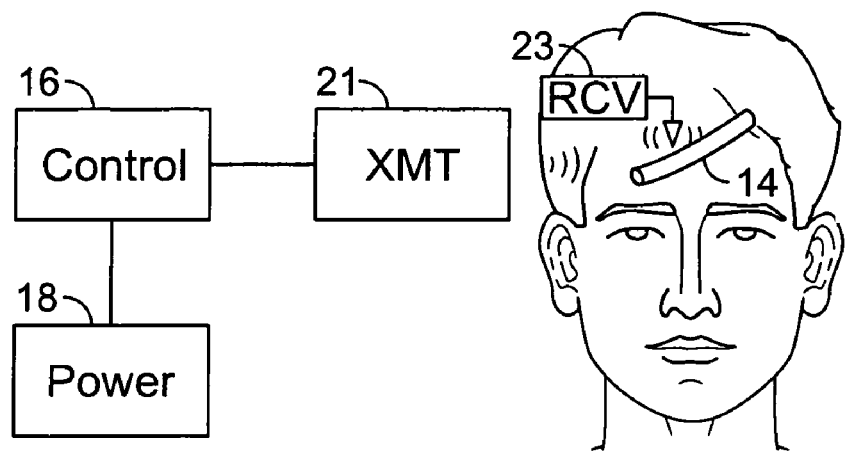
FIG. 3 is a wireless embodiment of the apparatus of FIG. 2.

The amplitude of the jamming signal depends in part on the type of actuator 12. In one embodiment, shown in FIG. 2, the actuator 12 includes a jamming electrode 20 that is implanted proximate to the vestibular nerve 14. In this case, the amplitude is selected such that a current on the order of a milliamp or less is present at the jamming electrode 20. Communication between the control unit 16 and the jamming electrode 20 can be established by a wire that perforates the skull. However, to avoid the need to perforate the skull, communication between the control unit 16 and jamming electrode 20 can also be wireless. This is achieved by a control unit 16 having a transmitter 21 and an actuator 12 having a receiver 23 in communication with the jamming electrode 20, as shown in FIG. [2.5]3.

Figure 4:
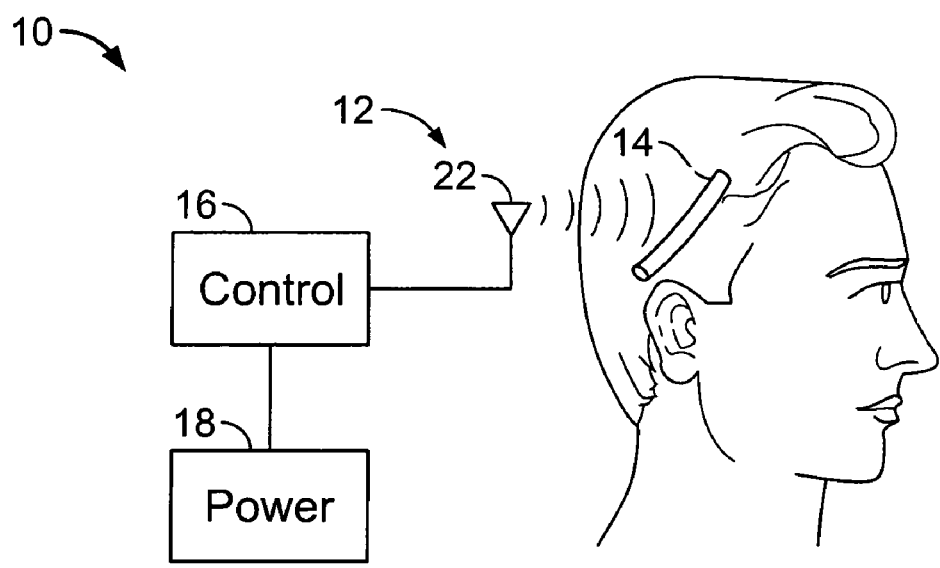
FIG. 4 is an embodiment in which the actuator of FIG. 1 is an antenna.

Another embodiment, shown in FIG. 4, avoids the need to implant by providing an actuator 12 that includes an antenna or external electrode 22 worn by the patient adjacent to the head. In this case, the amplitude is increased so that the vestibular nerve 14 is illuminated by sufficient power from the actuator 12. Typically, the amplitude is raised so that a current on the order of at least tens of milliamps is present on the antenna 22.

The jamming signal characteristics are selected such that the resulting combination of the jamming signal and the vestibular signal results in a signal having a constant pulse-repetition frequency. A time-varying signal of this type, the spectrum of which is essentially constant in time, will be referred to herein as a "stationary signal." In one embodiment, the pulse-repetition frequency is approximately equal to the maximum neuron firing rate, which is typically on the order of 450 Hz. This pulse-repetition frequency is likely to result in the synchronous firing of neurons at or near their maximum firing rate. However, it may be useful in some cases to have a much higher pulse-repetition frequency, for example in the 1-10 kilohertz range, so that neurons fire asynchronously.

The jamming signal need only be on during an attack of Meniere's disease. When the attack subsides, the jamming signal is removed and the patient regains normal vestibular function. The control unit 16 thus provides a mechanism for applying and removing the jamming signal.

In one embodiment, the control unit 16 has a patient-accessible switch 24, as shown in FIG. 1. When the patient feels the onset of an attack, he uses the switch to apply the jamming signal. A disadvantage of this type of control unit 16 is that because the jamming signal masks the symptoms of the attack, the patient is unable to tell whether the attack is over.

In the embodiment having a patient-accessible switch 24, the patient can simply use the switch to turn off the jamming signal after a reasonable time has elapsed. The resulting change in the pulse-repetition frequency of the signal received by the brain may result in some dizziness. However, if the attack of Meniere's disease is in fact over, this dizziness should fade shortly. If the dizziness does not fade, the patient uses the switch 24 to turn the jamming signal on again.

Alternatively, the switch 24 can include a timer that automatically turns the jamming signal off after the lapse of a pre-determined jamming interval. In some embodiments, the length of the jamming interval is user-controlled, whereas in others, the length of the jamming interval is hard-wired into the control unit 16. If the dizziness does not fade after the stimulation has been turned off, the patient uses the switch 24 to turn the jamming signal on again.

Figure 5:
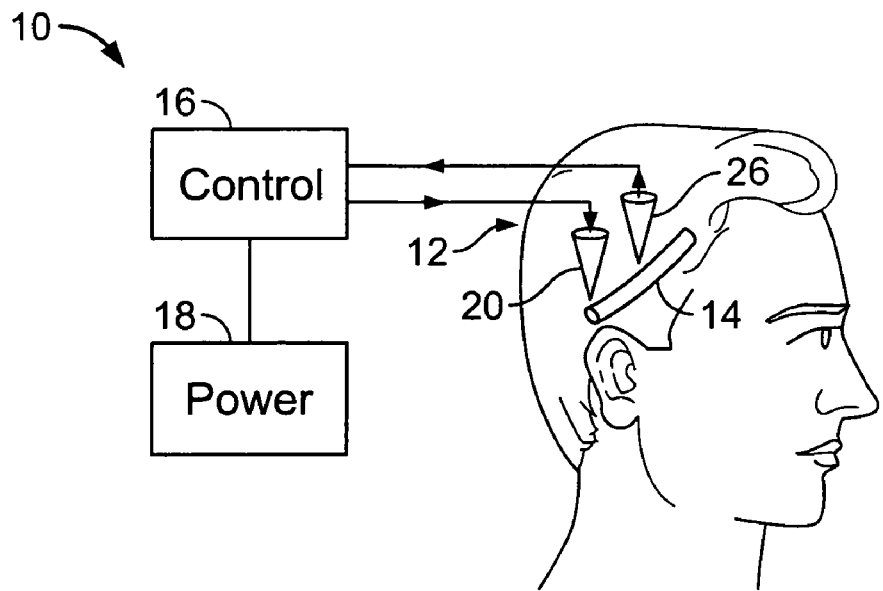
FIG. 5 is an embodiment having an automatic control unit with a feedback loop.

The control unit 16 can also be an automatic control unit 16 having a feedback loop, as shown in FIG. 5. In this case, a sensor electrode 26 is implanted proximate to the vestibular nerve 14 to measure the vestibular signal. When the control unit 16 detects appropriate time-varying changes in the pulse-repetition frequency of the vestibular signal, it causes the control unit 16 to apply the jamming signal to the jamming electrode 20. In this case, the jamming signal characteristics can be made to vary in response to the characteristics of the measured vestibular signal.

Figure 6:
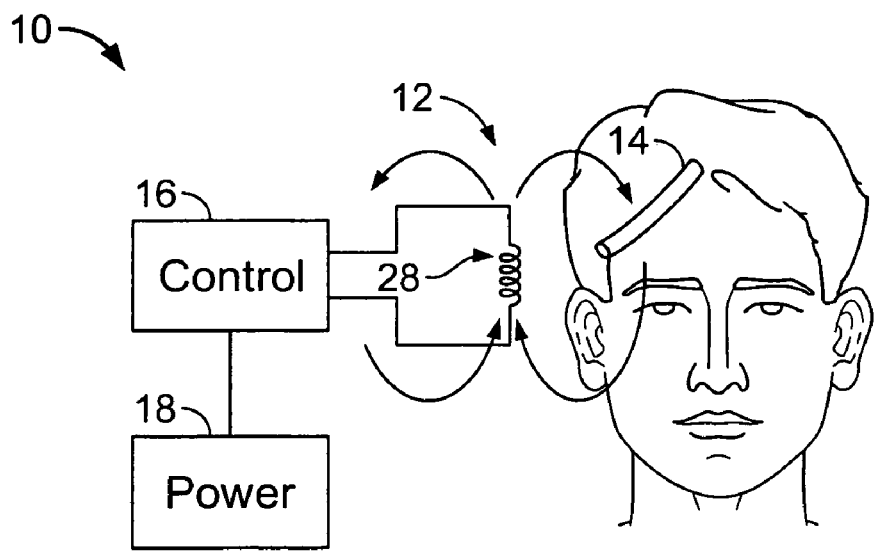
FIG. 6 is an embodiment in which the actuator of FIG. 1 is a coil for generating a magnetic field.

The jamming signal need not be an electrical signal. For example, in the embodiment of FIG. 6, the jamming signal is generated by a magnetic field generated by a coil 28 located outside the patient.

Figure 7:
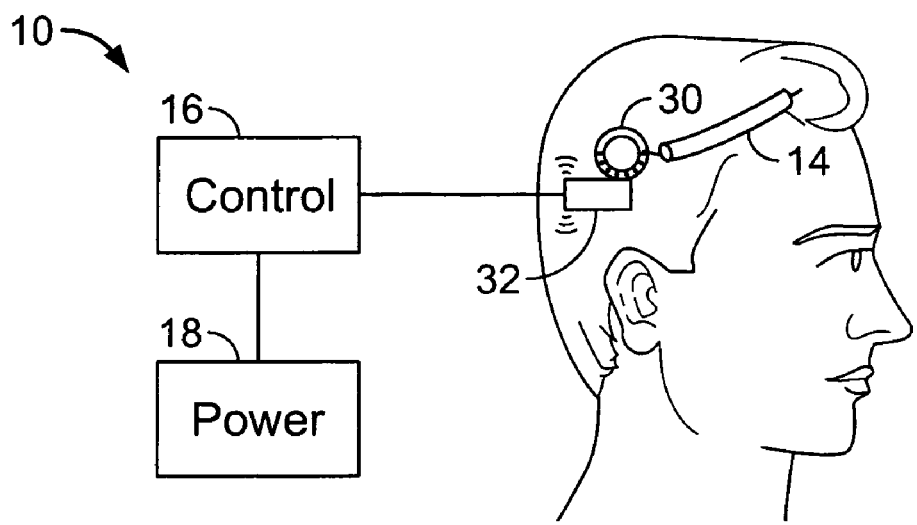
FIG. 7 is an embodiment having an actuator that shakes the vestibule.

Another embodiment, shown in FIG. 7, generates a jamming signal by mechanical stimulation of the vestibule 30. In this case, a piezoelectric element 32 is implanted proximate to the vestibule 30. The controller sends a jamming signal to the piezoelectric element 32, thereby causing the piezoelectric element 32 to flex and relax at a particular frequency. The motion of the piezoelectric element 32 is transmitted to the vestibule 30, thereby causing portions of the vestibule 30 to vibrate at that frequency. The vibration of the vestibule 30 causes the generation of an additional component of the vestibular signal. This additional component combines with the component resulting from the attack of Meniere's disease. Again, by proper selection of the pulse-repetition frequency, the signal received by the brain on the vestibular nerve 14 will again have a constant pulse-repetition frequency.

Figure 8:
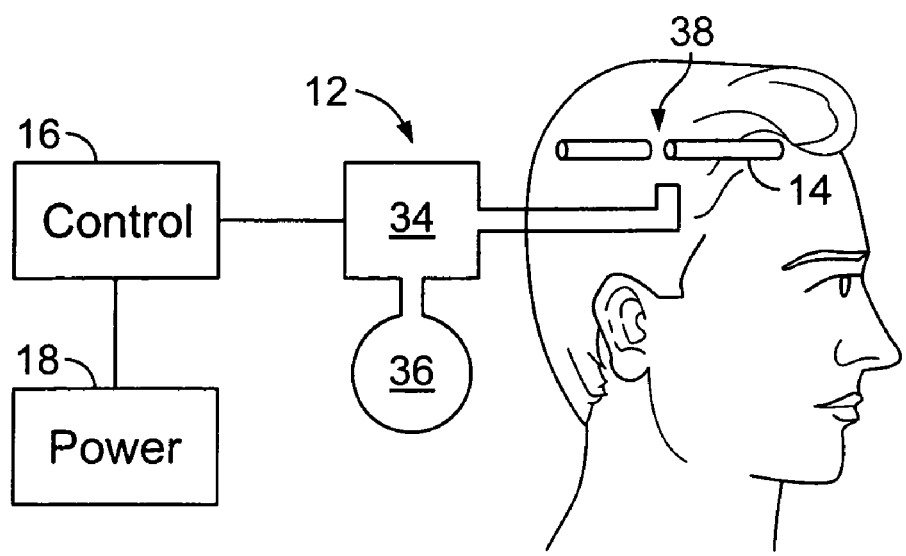
FIG. 8 is an embodiment in which an actuator applies chemical agents to the vestibular nerve area.

FIG. 8 shows an embodiment in which chemical agents interfere with the vestibular signal. In this case, the controller drives a pump 34 that pumps a chemical agent stored in a reservoir 36. The chemical agent can be a neurotransmitter to be administered to one or more synapses 38 at doses sufficient to drive repeated firing of the neurons at or close to their maximum firing rates. Again, this results in the generation of a jamming signal that interferes with, and effectively masks, the vestibular signal. Alternatively, the reservoir 36 can contain a neurosuppressive agent to be applied to the synapses to prevent the vestibular signal from reaching the brain. In this case, the vestibular signal that reaches the brain has a constant pulse-repetition frequency of zero.

The apparatus described herein has therapeutic purposes other than treatment of Meniere's disease. For example, the apparatus can be used to isothermally stimulate the vestibular system of a stroke victim afflicted with hemineglect. Such stimulation can provide relief from symptoms of hemineglect.

The foregoing embodiments of the apparatus all provide temporary and controllably reversible disabling of vestibular function by controllably jamming the vestibular signal with a jamming signal. Other embodiments are within the scope of the following claims:

The invention claimed is:

1. A method for providing relief from Meniere's disease to a patient in need thereof, the method comprising:
   detecting a symptom of an attack of Meniere's disease, and causing an actuator to cause the vestibular nerve to carry a pulse train following detection of the symptom of an attack of Meniere's disease,
   wherein the pulse train has a pulse repetition frequency selected to cause neurons in the vestibular nerve to fire synchronously relative to each other at a maximum neuron firing rate.

2. The method of claim 1 wherein causing the vestibular nerve to carry a pulse train comprises causing the actuator to carry a pulse train.

3. The method of claim 1, wherein causing an actuator to cause the vestibular nerve to carry a pulse train comprises exposing the vestibular nerve to a pulse train.

4. The method of claim 1, wherein causing an actuator to cause the vestibular nerve to carry a pulse train comprises mechanically stimulating the vestibule to cause a pulse train on the vestibular nerve.

5. The method of claim 1, wherein causing an actuator to cause the vestibular nerve to carry a pulse train comprises exposing the vestibular nerve to a chemical agent.

6. The method of claim 5, wherein exposing the vestibular nerve to a chemical agent comprises exposing the vestibular nerve to a neurotransmitter.

7. The method of claim 1, further comprising causing the actuator to stop causing the vestibular nerve to carry a pulse train.

8. The method of claim 1, where the pulse repetition frequency is selected to be on the order of 450 Hz.

9. The method of claim 1, wherein the pulse train is selected to cause a patient to perceive constant spatial orientation.

10. The method of claim 1, wherein causing an actuator to cause the vestibular nerve to carry a pulse train comprises receiving an input from a patient using a patient-accessible switch.

11. The method of claim 1, wherein causing an actuator to cause the vestibular nerve to carry a pulse train comprises receiving an input indicating onset of symptoms of Meniere's disease.

12. The method of claim 7, wherein causing the actuator to stop causing the vestibular nerve to carry a pulse train is carried out in response to a lapse of a time interval.

13. The method of claim 7, wherein causing the actuator to stop causing the vestibular nerve to carry a pulse train is carried out in response to a signal provided by the patient.

14. The method of claim 1, further comprising implanting the actuator proximate to the vestibular nerve.

15. The method of claim 14, further comprising providing a wire leading to the actuator through a perforation in a skull of the patient.

16. The method of claim 14, further comprising providing a wireless link to the actuator across a skull of the patient.

17. A method for providing relief from Meniere's disease to a patient in need thereof, the method comprising:
   receiving a first signal from the patient, in response to the first signal, causing an actuator to cause the patient's vestibular nerve to carry a pulse train,
   wherein the pulse train has a pulse repetition frequency selected to cause neurons in the vestibular nerve to fire synchronously relative to each other at a maximum neuron firing rate.

18. The method of claim 17, wherein causing an actuator to cause the patient's vestibular nerve to carry a pulse train comprises exposing the vestibular nerve to a pulse train.

19. The method of claim 17, wherein the pulse repetition frequency is on the order of 450 Hz.

20. The method of claim 17, further comprising causing the actuator to stop causing the patient's vestibular nerve to carry the pulse train.

* * * * *